(12) United States Patent
Bodmeier (10) Patent No.: US 7,927,618 B2
(45) Date of Patent: Apr. 19, 2011

(54) IMPLANTS, PARTICLES

(75) Inventor: Roland Bodmeier, Berlin (DE)

(73) Assignee: Laboratorios Farmacéuticos Rovi S.A., Madrid (ES)

( * ) Notice: Subject to any disclaimer, the term of this patent is extended or adjusted under 35 U.S.C. 154(b) by 1160 days.

(21) Appl. No.: 10/192,575

(22) Filed: Jul. 10, 2002

(65) Prior Publication Data

US 2004/0010224 A1  Jan. 15, 2004

Related U.S. Application Data

(63) Continuation of application No. PCT/DE01/00179, filed on Jan. 11, 2001.

(30) Foreign Application Priority Data

Jan. 11, 2000  (DE) .................................. 100 01 682
Jan. 11, 2000  (DE) .................................. 100 01 683

(51) Int. Cl.
*A61F 2/00* (2006.01)
*A61M 37/00* (2006.01)
*C08J 3/02* (2006.01)

(52) U.S. Cl. ............ 424/423; 604/84; 604/92; 523/113; 523/335

(58) Field of Classification Search .................. 604/82, 604/84, 56, 416, 518, 92; 424/422, 423, 424/426, 484, 486; 523/113–115, 333, 334, 523/223, 335
See application file for complete search history.

(56) References Cited

U.S. PATENT DOCUMENTS

| | | | |
|---|---|---|---|
| 4,188,373 A | 2/1980 | Krezanoski | 514/11 |
| 4,454,110 A | 6/1984 | Caslavsky | 424/54 |
| 4,865,585 A * | 9/1989 | Theeuwes | 604/85 |
| 4,938,763 A * | 7/1990 | Dunn et al. | 604/891.1 |
| 4,954,298 A | 9/1990 | Yamamoto et al. | 264/4.6 |
| 5,077,049 A | 12/1991 | Dunn et al. | 424/426 |
| 5,081,156 A | 1/1992 | Yamahira et al. | |
| 5,278,201 A | 1/1994 | Dunn et al. | 523/113 |
| 5,278,202 A | 1/1994 | Dunn et al. | 523/113 |
| 5,288,502 A | 2/1994 | McGinity et al. | |
| 5,324,519 A | 6/1994 | Dunn et al. | 424/426 |
| 5,324,520 A | 6/1994 | Dunn et al. | 424/435 |

(Continued)

FOREIGN PATENT DOCUMENTS

WO   WO 98/55100 A1   12/1998

OTHER PUBLICATIONS

U.S. Appl. No. 10/378,733, Bodmeier.

(Continued)

*Primary Examiner* — Kevin C Sirmons
*Assistant Examiner* — Catherine N Witczak
(74) *Attorney, Agent, or Firm* — Rick Matos; Innovar, L.L.C.

(57) ABSTRACT

This invention relates to kits for the preparation of a composition, which comprises a carrier phase that forms an implant or particles in the body, on the body or under physiological conditions. The carrier phase comprises at least one solid carrier material and a solvent, wherein the carrier material and the solvent are stored separately in the kit. The kit can also include an additional liquid phase to aid in forming the particles. An active compound included in the carrier phase is generally released in an extended manner. This invention also relates to compositions prepared from this kit and to methods for the preparation of the kits and the composition.

41 Claims, 1 Drawing Sheet

U.S. PATENT DOCUMENTS

| | | | |
|---|---|---|---|
| 5,336,180 A * | 8/1994 | Kriesel et al. | 604/82 |
| 5,340,849 A | 8/1994 | Dunn et al. | 523/113 |
| 5,368,859 A | 11/1994 | Dunn et al. | 424/426 |
| 5,487,897 A | 1/1996 | Polson et al. | 424/426 |
| 5,595,760 A | 1/1997 | Cherif-Cheikh | |
| 5,599,552 A | 2/1997 | Dunn et al. | 424/423 |
| 5,632,727 A * | 5/1997 | Tipton et al. | 602/47 |
| 5,639,796 A | 6/1997 | Lee | 514/773 |
| 5,654,008 A | 8/1997 | Herbert et al. | 424/489 |
| 5,681,873 A | 10/1997 | Norton et al. | 523/115 |
| 5,702,716 A | 12/1997 | Dunn et al. | 424/422 |
| 5,707,647 A | 1/1998 | Dunn et al. | 424/443 |
| 5,717,030 A | 2/1998 | Dunn et al. | 523/111 |
| 5,722,950 A | 3/1998 | Fujita et al. | 604/48 |
| 5,725,491 A | 3/1998 | Tipton et al. | 602/43 |
| 5,733,950 A | 3/1998 | Dunn et al. | 523/113 |
| 5,736,152 A | 4/1998 | Dunn et al. | 424/426 |
| 5,739,176 A | 4/1998 | Dunn et al. | 523/113 |
| 5,744,153 A | 4/1998 | Yewey et al. | 424/426 |
| 5,747,058 A | 5/1998 | Tipton et al. | 424/423 |
| 5,759,563 A | 6/1998 | Yewey et al. | 424/426 |
| 5,780,044 A | 7/1998 | Yewey et al. | 424/426 |
| 5,783,205 A | 7/1998 | Berggren et al. | 424/426 |
| 5,792,469 A | 8/1998 | Tipton et al. | 424/422 |
| 5,938,654 A * | 8/1999 | Wong et al. | 604/892.1 |
| 5,945,115 A | 8/1999 | Dunn et al. | |
| 5,980,945 A | 11/1999 | Ruiz | 424/484 |
| 6,413,784 B1 * | 7/2002 | Lundsgaard et al. | 436/518 |
| 6,796,966 B2 * | 9/2004 | Thomas | 604/191 |
| 2002/0090398 A1 | 7/2002 | Dunn et al. | |
| 2002/0177805 A1 * | 11/2002 | Barker et al. | 604/85 |
| 2003/0195489 A1 * | 10/2003 | Peterson | 604/500 |
| 2004/0127846 A1 * | 7/2004 | Dunn et al. | 604/82 |
| 2005/0192546 A1 * | 9/2005 | Griego et al. | 604/264 |

OTHER PUBLICATIONS

U.S. Appl. No. 09/445,311, Bodmeier.

R. L. Dunn et al., Sustained Activity and Release of Leuprolide Acetate from an In Situ Forming Polymeric Implant, AAPS PharmSciTech (2000), 1(1), article 1.

R. L. Dunn et al., Sustained Suppression of Pituitary-Gonadal Axis with an Injectable, In Situ Forming Implant of Leuprolide Acetate, J. Pharm. Sci. (Jun. 2000) 89(6), 732.

Material Safety Data Sheet for Leuprolide Acetate Injection, http:www.sicor.com/products/msds/leuprolide_acetate_inj_06.pdf (2005).

* cited by examiner

FIG. 1

IMPLANTS, PARTICLES

CROSS-REFERENCE TO EARLIER FILED APPLICATIONS

This application claims the benefit of PCT International Patent Application Serial No. PCT/DE01/00179 filed Jan. 11, 2001, which claims the benefit of German Patent Applications Serial No. 10001683.9 and Serial No. 10001682.0, both filed Jan. 11, 2000.

FIELD OF THE INVENTION

The present invention concerns kits, compositions, and methods for the formation of implants and/or particles in vivo. More particularly, the invention concerns an injectable composition that forms implants or particles when injected in a subject.

BACKGROUND OF THE INVENTION

Drugs can be administered parenterally as a depot formulation for the treatment of certain diseases. Besides classical dosage forms, such as oily suspensions, modern dosage forms on the basis of biocompatible/biodegradable polymers can be used. The implants (single-unit systems) or microparticles (multiparticulate systems) are prepared from the solid polymeric carriers and are then placed in the body by implantation or injection.

For the implant preparation, the drug is mixed with the carrier (e.g., a polymer) and is then processed into the desired implant shape (e.g., cylinder, pellet, film, fiber), for example by extrusion or compression at elevated temperatures. Such solid implants are then usually placed in the body by a surgical procedure or through hollow needles with a large diameter.

Drug-containing microparticles can be used in order to circumvent such surgical procedures with implants, which are highly undesired by patients. Suspensions of these particles can be injected with a syringe through an injection needle. These microparticles are prepared outside the body by various methods, such as for example the solvent evaporation, organic phase separation, or spray-drying techniques. In the solvent evaporation method, which is frequently used for the preparation of biodegradable microparticles, a drug is dissolved or dispersed in a solution of a biodegradable polymer (e.g., polylactic acid) in a solvent (e.g. methylene chloride), which is not miscible with water. This drug-containing polymer phase is then emulsified in an external aqueous phase and forms drug-containing polymer droplets. The microparticles are obtained after evaporation of the solvent through the solidification of the polymer and are then separated from the aqueous phase (e.g., by filtration) and dried.

Commercially available biodegradable microparticle products (e.g., Decapeptyl, Enantone) consist of a dry powder of the microparticles and an aqueous suspension vehicle. The microparticles and the aqueous suspension vehicle are stored separately, for example in multi-chamber (having two or more chambers) syringes or in two ampoules, because of the hydrolytic instability of the biodegradable polymers. The microparticles are then suspended in the aqueous suspension vehicle just prior to the administration and are then injected. The preparation of these biodegradable particle products is very elaborate and has to be done under sterile or aseptic conditions. In addition, most microencapsulation techniques are difficult or not at all transferable to the production size and are dependent on many process- and formulation variables. The suspension of the microparticles and the subsequent injection can also cause difficulties (e.g., agglomeration, residual microparticles in the syringe, clogging of the needle, etc.).

Aside from the water-insoluble polylactic acid derivatives and other water-insoluble polymers, hydrophilic polymers can also be used as carrier materials for microparticles and implants. Microparticles of hydrophilic polymers (e.g., polysaccharides, such as alginates or chitosan, cellulose derivatives, protein—(collagen) derivatives) can be prepared for example through spray-drying or w/o-emulsification techniques, whereby the drug-containing aqueous polymer solution is either spray-dried or emulsified into an external oil phase, whereby the particles are obtained after removal of the water, washing, filtration and drying. Like the techniques for the preparation of polylactic acid microparticles, the microencapsulation techniques with the hydrophilic polymers are also very elaborate.

U.S. Pat. No. 4,938,763 discloses a composition based on a drug-containing polymer solution. The composition was developed in an attempt to avoid problems with the preparation and administration of implants or microparticles. A solution of polylactic acid (or a derivative) is injected into the body, for example intramuscularly, subcutaneously, or periodontally and an implant is formed in-situ through the precipitation of the polymer in the tissue and the drug is then released slowly. The implant is therefore not formed outside, but inside the body. The drug is either dissolved or dispersed in the polymer solution, or in the case of stability problems, it is stored separately from the polymer solution. The preparation of this composition is much easier than the preparation of conventional implants or microparticles. A commercial product based on this in-situ implant technology (Atrigel-technology) is already available in the USA and is in the approval process in Europe. This product has the trade name ATRIDOX and is used for the periodontal administration of doxycycline. The drug doxycycline and the polymer solution (consisting of the polymer, poly(dl-lactide) dissolved in the solvent N-methyl-2-pyrrolidone) are separately stored in two syringes because of stability reasons. The drug and polymer solution are mixed shortly before administration through a connector, which connects both syringes, by forward-and-backward pushing of the syringe plungers and are then administered. A 200-times forward-and-backward pushing of the plungers is necessary in order to obtain a good distribution of the drug in the polymer solution prior to administration. It is important to note that the ATRIGEL system requires the preformation and storage of a polymer solution in a syringe. The polymer used is not a fast dissolution rate polymer nor is it a highly soluble polymer and thus requires large amounts of solvent in preparing the polymer solution. The polymer takes several hours and even up to a full day to dissolve.

Other systems have been developed, whereby a solidification/viscosity increase of drug-containing polymer solutions after administration/injection in the body was caused primarily by a temperature- or pH-change or by special substances (e.g., ions), and not by diffusion of the solvent. These systems have the same disadvantages as the systems described in the previous two paragraphs. The polymer solution has to be injectable through a needle, it therefore cannot be too viscous. The possible polymer content is therefore primarily limited by the viscosity of the polymer solution and not through the solubility of the polymer. In addition, precipitation of the polymer during the injection of the polymer solution can negatively influence the injection of the remaining polymer solution. Disadvantages of this method are also the use of high amounts of solvents having toxicity and compatibility problems and, after injection into soft tissue, the somewhat uncontrollable solidification of the polymer resulting in an undefined surface area of the implant. This can lead to irreproducible release profiles. In addition, the drug can be released rapidly prior to the solidification of the polymer solution. This so-called burst-effect is usually undesirable.

WO 98/55100 describes compositions, which are easy to prepare and which avoid problems obtained during the development and administration of microparticles and implants, including the described in-situ implants. These compositions form particles and/or implants after placement in the body and are obtained after mixing an inner polymer-containing carrier phase with an immiscible or partially immiscible second external phase, whereby the viscosity of the carrier phase is changed after a change in ambient conditions. For example, an active compound-containing dispersion, comprising an inner carrier phase and a second external phase (e.g., an oil) may be prepared and be placed into the body. The inner phase then solidifies, for example through solvent diffusion in the environment or diffusion of body fluids into the carrier phase, or through a change in temperature, pH-value or ionic strength. The carrier material is dissolved in a solvent and present as a solution in its packaging material. The carrier material is not present as a solid. For example, in the case of biodegradable polymers, the dispersion may be injected i.m. or s.c., in the case of peroral administration, the liquid dispersion can be filled into capsules. The inner phase can solidify in contact with body fluids and can form, for example, particles. The carrier phase can also be mixed with the second external phase just prior to administration. This can be required, if the dispersion is physically unstable, which means that the internal carrier phase separates from the second external phase.

U.S. Pat. No. 5,081,156 discloses an injectable composition that is an oily suspension of drug-collagen particles. The composition does not form an implant or particles although it is reconstituted prior to use. The carrier material does not harden after injection into a subject and the carrier material is not dissolved after reconstitution of the suspension.

U.S. Pat. No. 5,595,760 discloses an injectable composition wherein a peptide drug gels in a subject after injection of the composition into the subject. The carrier material used does not solidify and does not provide an extended release of drug as the longest release period achieved is about 3 hours. This patent does not disclose the formation of an implant or particles.

Aside from chemical stability, physical stability plays an important role with liquid dispersed systems, for example with drug suspensions in polymer solutions. During storage of prior art systems, sedimentation and the formation of a non-redispersible cake can occur.

Thus, none of the known art discloses a system for the formation of implants or particles in vivo wherein the implant or particles provides an extended release of drug, the carrier material is dissolved in a solvent just prior to use, the carrier material is present as a solid in a kit, and the carrier material hardens in a subject after injection.

SUMMARY OF THE INVENTION

The present invention seeks to overcome some or all of the disadvantages inherent in the art. The present invention provides a kit for the in situ formation of an implant or particles in a subject after exposure of a carrier phase to physiological conditions or a physiological environment, for example by placing the composition within or in contact with the subject. The kit includes a solid or semisolid carrier material and a solvent that are separate during storage and mixed just prior to use.

Surprisingly, it has been found that the carrier phase can be prepared just prior to administration. The polymer (carrier material) used herein is mixed with a solvent just prior to administration and is therefore not stored in the form of a polymer solution, which is the final carrier phase. A composition according to the invention does not consist of a pre-stored polymer solution (like in the above described in-situ implant system), but for example, of a solid polymer in one syringe and, separately from the polymer, a solvent in a second syringe. Just prior to administration, the polymer is mixed with the solvent through a connector, which combines the two syringes, by pushing the syringe plungers forward and backward and the polymer is at least partially brought in solution. Therefore, the polymer solution is formed just prior to administration of the injectable composition in a subject.

The kit of the invention contains the carrier material (e.g., a polymer) in solid or semisolid form. The solid carrier material is separately stored from the solvent. The carrier material is dissolved within minutes in the solvent just prior to administration. A small quantity of polymer is dissolved in a small quantity of solvent (normally less than 2 ml), which is then injected. The polymer solution according to the invention is prepared for an individual unit to be administered immediately or shortly after preparation.

If necessary, this mixture can be dispersed in an additional liquid phase (for example, through a connector with a third syringe, which comprises the external phase) and then be administered. The carrier material and the solvent can also be mixed within a multi-chamber syringe and then, if necessary, be dispersed through a connector in an additional liquid phase (which is present in a second syringe). Several mixing options are possible for the preparation of the dispersion. The carrier phase is the inner phase and the additional liquid phase is the outer phase of this dispersion which is in the form of droplets. The droplets form particles or an implant under physiological conditions, and the droplets harden into particles. In other words, an implant is usually formed from the administration of the carrier phase in the absence of an additional liquid phase, while particles can be formed from a dispersion comprising an inner carrier phase, which forms the particles, and the external additional liquid phase.

A separate storage of the polymer and solvent in the final product and the preparation of the carrier phase just prior to administration has several advantages when compared to the storage of a polymer solution. An important point thereby is the stability of the dosage form, which includes the chemical stability of the drug and excipients (for example the polymer) during storage. The drug and/or the polymer can degrade when present in dissolved form during storage. In particular, macromolecular drugs (e.g., peptides or proteins) or also polymers and other excipients often contain non-negligible amounts of water, which affect the stability, in particular of biocompatible, hydrolytically degradable polymers, negatively. The molecular weight of the polymer can change during storage in the liquid state, this can obviously affect the drug release and can lead to unacceptable changes in the drug release and therefore also in the pharmacological action. An additional advantage of this invention is that storage at low temperatures is usually not necessary. Moreover, the drug and polymer can be incorporated into the solvent in a single step, such that the elaborate preparation of the polymer solution is eliminated.

It is an object to eliminate or reduce the occurrence of stability problems that typically accompany liquid, drug-containing carrier material solution formulations. The invention provides a composition for the formation of implants and/or particles, the composition comprising at least one carrier material and one solvent, which is separated from the carrier material, wherein the carrier material is mixed with and at least partially dissolved in the solvent just prior to administration, and wherein this mixture (if necessary, after dispersion in an additional immiscible or partially not miscible liquid external phase) forms an implant and/or particles after administration in or on the body.

The invention provides a kit for the preparation of a composition, which comprises a carrier phase, which forms an implant or particles in the body or on the body under physiological conditions, whereby the carrier phase comprises at least one carrier material and a solvent, and wherein the carrier material and the solvent are separated from each other in the kit. The kit comprises a combination of at least 2 components (e.g., a carrier material and solvent), which are used for the preparation of the composition and which are added to each other with appropriate tools. The individual components and the tools (e.g., syringes) are normally packaged in a secondary package.

The invention also provides a method of forming in situ an implant or plural particles by mixing a carrier material and solvent to form a carrier phase containing the carrier material in completely dissolved or incompletely dissolved form. The carrier phase is then placed within or on a subject (body) at which time the implant or particles start to form. Any active compound present is also present within the carrier phase. The implant or particles provide an extended release of active compound after formation of the implant or particles.

One aspect of the invention provides a kit for the preparation of a composition comprising a carrier phase, which forms an implant or particles in a body, on a body or under physiological conditions, the kit comprising:
  at least one solid or semisolid carrier material; and
  a solvent for the carrier material, wherein the carrier material is separate from the solvent;
  wherein at least a portion of the carrier material dissolves in the solvent, if placed in contact therewith, thereby rapidly forming an administrable carrier phase.

Another aspect of the invention provides a method for the preparation of a kit, the method comprising the steps of:
  including a carrier material in solid or semisolid form in a syringe or in a chamber of a multi-chamber syringe; and
  including a solvent for the carrier material in a separate syringe or separate chamber of the multi-chamber syringe;
  wherein the solvent can at least partially dissolve the carrier material if the two are mixed to rapidly form an administrable carrier phase.

Still another aspect of the invention provides a method for the preparation of an implant or particulate composition, the method comprising the steps of:
  storing a carrier material and solvent in separate syringes or separate compartments of a multi-compartment syringe;
  mixing the carrier material and solvent such that the carrier material is at least partially dissolved in the solvent thereby forming an administrable carrier phase; and
  administering the carrier phase by placing it within or on a subject or by exposing it to a physiological condition thereby forming the implant or particulate composition.

Specific embodiments of the invention include those wherein: 1) the carrier material comprises a water-soluble polymer, a water-insoluble polymer, a polymer that is soluble in aqueous fluids, a biocompatible and/or biodegradable polymer, a protein, a lipid, a non-polymeric material or a combination thereof; 2) the carrier material and the solvent are stored in separate syringes or in separate chambers of a multi-chamber syringe such that when the carrier material is mixed with the solvent, prior to administration, through a connector or within a multi-chamber syringe, the carrier material is at least partially dissolved in the solvent; 3) the carrier material comprises a poly(lactide) or poly(lactide)-derivative or copolymer, a monoglyceride, sucroseacetate-isobutyrate or a combination thereof; 4) the composition forms cubic or liquid crystalline phases in the body, on the body or under physiological conditions; 5) a portion of the carrier material is present in the solvent prior to mixing of the solvent with the solid carrier material; 6) the composition further comprises at least one active compound; 7) the active compound is encapsulated; 8) the composition further comprises a viscosity-modifying substance, stabilizer, release modifying agent, pore-former, substance that changes the residence time of the active compound or composition at a site of administration, bioadhesive material, penetration enhancer, substance for the retardation of the release of active compound, substance for the avoidance of a rapid initial release of active compound at a site of administration or a combination thereof; 9) the composition is adapted for parenteral, peroral, subcutaneous, rectal, buccal, ophthalmic, pulmonary, vaginal, nasal, local, sublingual, periodontal, or transdermal administration, for application into a body cavity or for application onto a body surface; 10) the composition is adapted for the treatment of soft- and hard tissue defects, treatment of tissue regeneration, use as glue, filling of a body cavity, or the treatment of a wound; 11) the composition further comprises an additional liquid phase in which the carrier phase is dispersed; 12) the additional liquid phase is stored in the kit separate from the carrier material and the solvent, is in contact with the carrier material and separate from the solvent, or is in contact with the solvent and separate from the carrier material; 13) the at least one active compound is present together with one or more of the carrier material, solvent or additional liquid phase; and/or 14) the implant or particles provide an extended release of active compound when placed in the body, on the body or under physiological conditions.

DETAILED DESCRIPTION OF THE INVENTION

The terms "implant" or "particle" refer to a viscous liquid, semisolid and/or solid present in any shape, size, consistency, and structure. It can be administered in any site in a subject. The term is not only used for compositions administered in the body, but also for compositions administered on the body. For example, films can be formed by spraying or applying the composition to the body. The implant and/or particles form from the composition after body contact, for example through an increase in concentration or precipitation of the carrier material, through a diffusion of the solvent away from the carrier phase, through a contact with body fluids, through a temperature- or pH-change, through substances present at the site of administration, through a change in ionic strength or type of ion, or through a combination of these factors. The implant and/or particles can also be formed outside and not in contact with the body. A composition according to this invention is formed into a shape after mixing the carrier material with the solvent and is then hardened in contact with aqueous fluids into this preformed shape. These externally formed implants and/or particles can also be placed in or onto the body. In one embodiment, the implant is formed by contacting the polymer solution with an aqueous fluid to precipitate the polymer into an externally formed implant or particles that are then implanted/injected.

The carrier material and the solvent are stored separately in syringes or within a multi-chamber syringe, and the carrier material is mixed with the solvent just prior to administration through a connector (which connects both syringes). The carrier material is at least partially dissolved in the solvent. The carrier material can be placed in dry form (e.g., as powder) in a syringe or a chamber of the two-chamber syringe, or the carrier material can be placed as a solution or a dispersion in a syringe or a chamber of a two-chamber syringe and is subsequently dried therein, for example by lyophilization. The carrier material and the solvent can also be stored separately in other containers (e.g., ampoules or glass vials). The carrier material forms the matrix of the implant/particle and is important for the retardation of the release of the active compound with active compound-containing compositions.

The carrier material comprises a water-soluble polymer, a water-insoluble polymer, a polymer, which is soluble in aqueous fluids, a biocompatible and/or biodegradable polymer, a protein, a lipid, a non-polymeric material or a combination of these carrier materials.

It is preferred that the carrier material be a poly(lactide) or poly(lactide)-derivative, or that the carrier material comprise a monoglyceride (e.g., glycerolmonoglyceride, -linoleate), which forms a liquid crystalline phase, for example a cubic phase, after administration in or on the body.

The carrier material can comprise synthetic, semisynthetic or natural materials. Exemplary materials include cellulose derivatives (e.g., cellulose acetate, ethyl cellulose, cellulose acetatephthalate, cellulose ethers such as hydroxypropylmethyl cellulose), acrylate-derivatives (e.g., Eudragit, poly(methylmethacrylate), cyanoacrylate) and also biocompatible and biodegradable polymers like polyanhydrides, polyesters, polyorthoesters, polyurethanes, polycarbonates, polyphosphazenes, polyacetals and polyoxyethylene-oxypropylene. Important are thereby polyesters such as polylactide, polyglycolide, polycaprolactone, polyhydroxybutyrate- or valerate. In addition, polysaccharides such as sodium alginate, chitosan, or chitin or proteins may be used. Nonpolymeric carrier materials are for example sucroseacetateisobutyrate, disaccharideesters. A great number of carrier materials are described in the literature, they are all potentially useful for compositions according to this invention.

According to the invention, the solvent is water or an organic solvent, such as ethanol, acetone, butanol, ethylformate, acetic acid, pentanol, n- or iso-propanol, tetrahydrofuran, triethylcitrate, triacetin, propylene glycol, glycerol, polyethylene glycol, acetone, ethylacetate, methylacetate, ethyllactate, benzylalcohol, dimethylformamide, dimethylsulfoxide, dimethylacetamide, propylenecarbonate, glycofurol, oleic acid, 2-pyrrolidone, N-methyl-2-pyrrolidone, or an oil or a plasticizer or a mixture of two or more of these solvents.

In particular, solvents listed in the "draft guideline of the international conference on harmonization on impurities—residual solvents" may be used. The solvent should dissolve the carrier material to some extent. Combinations of solvents and nonsolvents can also be used for the carrier material. Solvent mixtures can also be used, selected for example with regards to the solvent quality for the carrier material or miscibility with aqueous phases. For example, the solvent selection can influence the rate of dissolution of the carrier material and the miscibility with body fluids. Solvents miscible with body fluids will diffuse faster from the site of administration when compared to solvents, which are not or are only partially soluble with body fluids. This will affect the hardening process of the implant or of the particles under physiological conditions and therefore the microstructure or porosity of the implant or particles, which will affect the release of the active compound. Solvents miscible with body fluids potentially result in faster hardening and more porous implants or particles, which could affect the drug release. More porous structures release the active compound faster. The solvent may or may not be only partially miscible with the additional liquid phase. This additional liquid phase forms the external phase of a dispersion consisting of the carrier phase (internal phase) and the additional liquid phase (outer or external phase). The viscosity of the carrier phase can be influenced by the carrier material (e.g., molecular weight, concentration, etc.) and by the solvent. The viscosity of the carrier phase is higher when using higher molecular weight carrier materials of same chemical structure and at higher concentration of the carrier material. These parameters also affect the structure of the implant or particles. For example, the release of the active compound is slower at higher concentrations of the carrier material in the carrier phase.

The rate of dissolution of the carrier material in the solvent depends on many factors, for example on the quality of the solvent for the carrier material, on the particle size, the molecular weight, the porosity and the concentration of the carrier material, the temperature and on the mixing intensity. A fast rate of dissolution is usually desirable because the carrier phase can then be administered faster. The carrier material dissolves faster in a good solvent than in a poor solvent. The carrier material can be obtained in powder form through various methods. For example, porous particles can be obtained by spray-drying solutions of the carrier material (e.g., polymer solutions). Smaller particles can be obtained through grinding. Smaller particles of the carrier material dissolve faster than larger ones. Lyophilization of polymer solutions results in a porous sponge (for example in a syringe or a two-chamber syringe) or in a porous powder. Because of its low density, this porous sponge dissolves very rapidly after the addition of a solvent. A higher porosity of the powder or lyophilized sponge, a smaller particle size of the carrier material, a lower carrier material concentration in the solvent and a higher mixing intensity usually result in a faster rate of dissolution of the carrier material. A higher porosity of the sponge can for example be obtained by freeze-drying more dilute carrier material solutions or with faster freezing rates. A composition according to this invention can therefore be administered very rapidly. This dissolution process can occur in less than a minute up to several minutes after bringing the carrier material in contact with the solvent. Even though dissolution of the polymer may be incomplete, a sufficient portion (generally at least 25% wt., at least 50% wt., at least 75% wt.) of the carrier material will dissolve in the solvent within, i.e., will have a dissolution period of, less than about 60 min, 30 min, 20 min, 10 min, 5 min, or 1 min. thereby rapidly forming an administrable carrier phase comprising partially or completely dissolved carrier material. As opposed to prior art systems, the system of the invention is adapted for rapid use such that the just formed polymer solution will form shortly after mixing of the carrier material and solvent.

A part of the carrier material can be present in the solvent. A part of the carrier material can also be dissolved in the solvent, if the carrier material can be stored in a stable form in the solvent. This can lead to a faster reconstitution of the remaining carrier material and therefore to a faster administration.

The additional liquid phase is fully or partially miscible or immiscible with aqueous fluids, and the additional liquid phase is stored separately from the carrier material and the solvent, or is stored in contact with the carrier material and separated from the solvent, or in contact with the solvent and separated from the carrier material, or in a combination of one of these alternatives.

The additional liquid phase comprises natural, semisynthetic or synthetic lipids, oils or waxes, such as cottonseed oil, soybean oil, safflower oil, hydrated peanut oil, olive oil, castor oil, triglyceride mixtures (like Miglyol), silicone oil, isopropylmyristate, ethyloleate, paraffins, water, glycerol, propylene glycol or polyethylene glycol or mixtures of two or more of these substances.

According to the invention, the composition comprises an active compound, the active compound is a drug, a peptide- or protein drug (e.g., LHRH-agonists and -antagonists, insulin, somatostatin, interleukins, interferons, growth hormones, erythropoetin), an oligonucleotide or gene therapeutic agent, the drug belongs to the group of antibiotics, anti-inflammatory agents, antiinfectives, hormones, immunologically active compounds, vaccines, immunomodulators, immunosuppressant, anticancer agents, diuretics, compounds for the gastrointestinal tract, for the heart/circulation, for the respiratory tract, growth factors, analgesics, local anesthetics and/or neuropharmaceuticals, or that the drug is tetracycline or doxycycline. The active compounds can comprise low or higher molecular weight drugs for human- and veterinary administration and substances, which are used for agricultural purposes, in households, in the food, cosmetic and chemical industry and other industrial branches.

Active compounds preferably include physiologically or pharmacologically active substances that produce a systemic or localized effect or effects on animals and human beings. Active compounds also include pesticides, herbicides, insecticides, antioxidants, plant growth instigators, sterilization agents, catalysts, chemical reagents, food products, nutrients, cosmetics, vitamins, sterility inhibitors, fertility instigators, microorganisms, flavoring agents, sweeteners, cleansing agents and other such compounds for pharmaceutical, veterinary, horticultural, household, food, culinary, agricultural, cosmetic, industrial, cleaning, confectionery and flavoring applications. The active compound can be present in its neutral, ionic, salt, basic, acidic, natural, synthetic, diastereometric, isomeric, enantiomerically pure, racemic, hydrate, chelate, derivative, analog, or other common form.

The active compound can be independently selected at each occurrence from active agents such as an antibiotic agent, antihistamine agent, decongestant, anti-inflammatory agent, antiparasitic agent, antiviral agent, local anesthetic, antifungal agent, amoebicidal agent, trichomonocidal agent, analgesic agent, anti-arthritic agent, anti-asthmatic agent, anticoagulant agent, anticonvulsant agent, antidepressant agent, antidiabetic agent, antineoplastic agent, anti-psychotic agent, neuroleptic agent, antihypertensive agent, hypnotic agent, sedative agent, anxiolytic energizer agent, antiparkinson agent, muscle relaxant agent, antimalarial agent, hormonal agent, contraceptive agent, sympathomimetic agent, hypoglycemic agent, antilipemic agent, ophthalmic agent, electrolytic agent, diagnostic agent, prokinetic agent, gastric acid secretion inhibitor agent, anti-ulcerant agent, anti-flatulent agent, anti-incontinence agent, cardiovascular agent or a combination thereof.

A composition according to the invention releases the active compound in an extended (retarded, slow, controlled, or sustained) manner at the site of administration. The release of the active compound may be influenced for example through the degree of dispersity, the loading of the active component, the carrier material and the concentration of the carrier material. The drug release is generally slower with increasing concentration of the carrier material in the carrier phase, higher molecular weight of the carrier material and lower drug loading in the carrier phase with hydrophilic drugs. In the case of dispersions, the drug release is increased with a smaller particle size of the internal carrier phase. In addition, release modifying agents, such hydrophilic or lipophilic substances of inorganic, organic or polymeric nature can also be incorporated. A special advantage of the dispersions is, that, in comparison to active compound-containing polymer solutions, which form an implant in-situ, an initial rapid release of the active component may be avoided at the site of administration. The active component-containing carrier phase represents the internal phase of the composition and is therefore not primarily in contact with the surrounding body immediately after administration.

The active compound can be encapsulated, for example, in particles. The term "particle" in this context (to be distinguished from particles, which form from the carrier phase) is broad and comprises for example microparticles, microcapsules, colloidal particles (e.g., nanoparticles, nanocapsules, liposomes), compounds bound to ion exchange resins, cyclodextrins. The material used for encapsulation can be of polymeric as well as of nonpolymeric origin (e.g., lipids). By combining the particles with the implant, the retardation of the release can be prolonged or the burst-effect (initial rapid release) can be reduced/eliminated. For example, incorporating the encapsulated active compound (e.g., microparticles) in a composition according to the invention can avoid an often undesired rapid initial release of the active compound. The solvent for the carrier material should not dissolve the encapsulation material or should dissolve it slower than the carrier material. Encapsulation- and carrier material can be from the same chemical group of substances, for example, in the case of polymers, they can differ in molecular weight or monomer ratio.

The active compound can be mixed with the carrier material, or can be dissolved and/or dispersed in the solvent/solvent mixture, or can be present in both. For example, a powdery active compound can be filled together with the powdery carrier material in a container (e.g., a syringe), both active compound and carrier material are then present in solid form. The active compound can also be dissolved or dispersed in a solution of the carrier material, this liquid is then filled in a container and dried, for example by lyophilization. In these cases, the active compound and the carrier material are therefore together, but separated from the solvent. In particular, after the concomitant lyophilization of a liquid active compound-carrier material phase, the active compound is homogeneously incorporated into the carrier material, which results then in a rapid, uniform distribution of the active compound after addition of the solvent. Alternatively, the active compound can be stored only in the solvent or together with the solvent and carrier material.

The composition can comprise viscosity-modifying substances, stabilizers, release modifying agents, pore-formers, substances, which change the residence time at the site of administration, bioadhesive materials and/or penetration enhancers, wherein the active compound is released prolonged at the site of administration and/or wherein the initial rapid release of the active compound at the site of administration is avoided. Stabilizers, such as emulsifying agents, may be necessary for the preparation of the dispersion with an additional liquid phase. The emulsifying agents include among others polyethyleneglycol-fatty acid esters, -fatty acid ethers, -sorbitan fatty acid esters, sorbitan fatty acid esters, partial fatty acid esters of multivalent alcohols or sugars, lecithins and poloxamers.

The invention includes compositions for the parenteral (e.g., i.m., s.c., i.a.), peroral, subcutaneous, rectal, buccal, ophthalmic, pulmonary, vaginal, nasal, local, sublingual, periodontal, or transdermal administration and/or for the application into body cavities and/or for the application onto body surfaces. The composition can also be used for the treatment of soft- and hard tissue defects, for example as scaffolding, for tissue regeneration, as glue, or for the filling of body cavities, or for the treatment of wounds. In the case of internal or external wound treatment, a composition according to the invention can be placed onto various, medically used, textile fabrics prior to administration.

The composition can be administered in body cavities or on body surfaces by methods known to the person skilled in the art (e.g., by injection or by spraying-on or -in).

The invention includes methods for the preparation of compositions according to the invention, whereby at least one carrier material is mixed with and at least partially dissolved in the solvent just prior to administration, and whereby this mixture (if necessary, after dispersion in an additional immiscible or partially miscible liquid external phase) forms an implant and/or particles after administration in or on the body.

The invention also includes methods, whereby the carrier material and the solvent are stored separately in syringes, and whereby the carrier material is mixed with the solvent through a connector and is at least partially dissolved, or includes methods, whereby the carrier material and the solvent are stored separately in a two-chamber syringe and whereby the carrier material is mixed with and at least partially dissolved in the solvent within the two-chamber syringe.

This invention includes kits for the preparation of compositions according to this invention, whereby the carrier material is mixed with and at least partially dissolved in the solvent just prior to administration, and whereby this mixture (if necessary, after dispersion in an additional immiscible or partially not miscible liquid external phase) forms an implant and/or particles after administration in or on the body.

Figure 1:
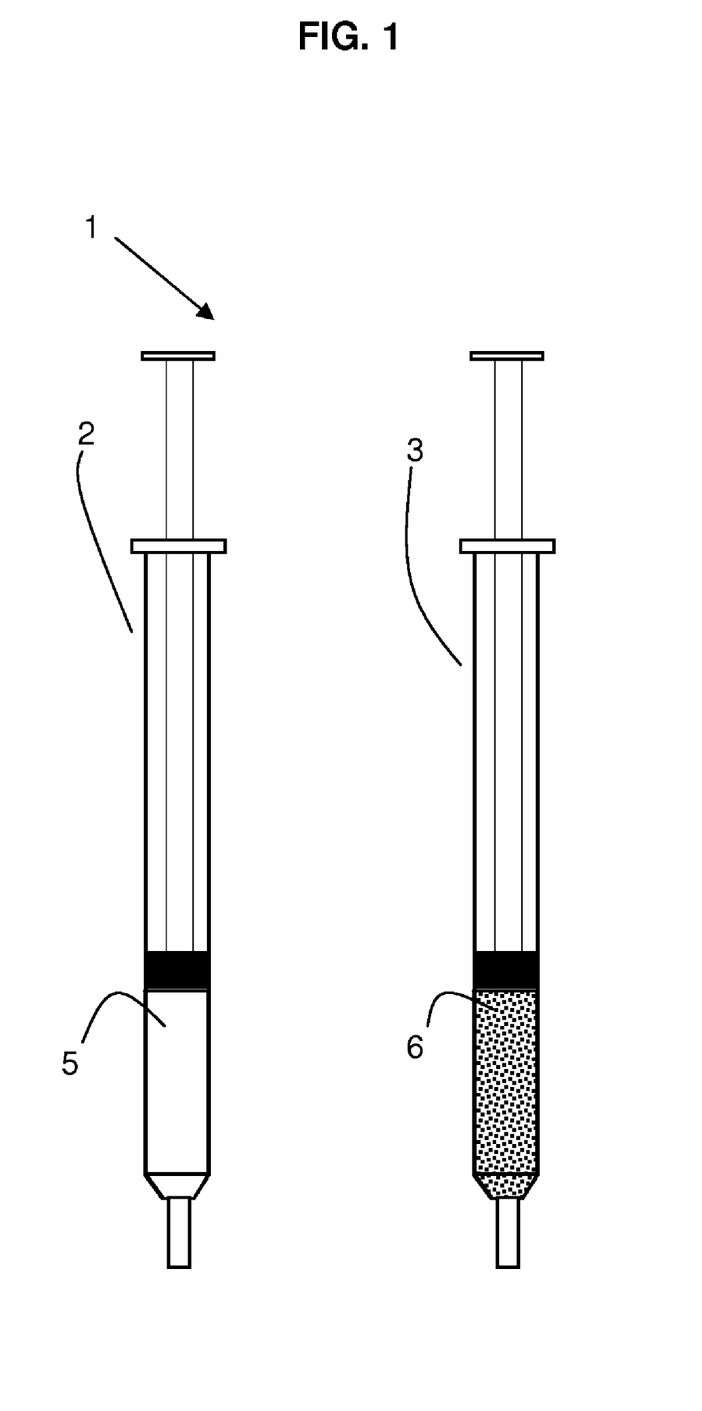

The invention also includes kits (1, FIG. 1), wherein the carrier material (6) and the solvent (5) are stored separately in syringes (3, 2, respectively) or in a two-chamber syringe.

The kit comprises at least two components in at least one packaging to be used together.

The invention includes implants and/or particles, which are obtained with the described compositions, methods and kits.

The final product or embodiment of the invention, for example as provided commercially, contains the polymer in solid and not in already dissolved form during storage. The polymer is stored separately from the solvent, for example in a two-chamber syringe or in two separate syringes or ampoules. The polymer solution (and, if necessary, the dispersion in an additional liquid phase) is therefore not prepared by the manufacturer, but by the user (e.g. medically trained personal) just prior to administration to the patient.

A commercial product of a composition according to the invention will comprise a carrier material, which is separated from the solvent, and a solvent.

It should be understood, that compounds can generally serve a variety of functions or purposes. Thus, if a compound named herein is mentioned only once or is used to define more than one term herein, its purpose or function should not be construed as being limited solely to that named purpose(s) or function(s).

In view of the above description and the examples below, one of ordinary skill in the art will be able to practice the invention as claimed without undue experimentation. The foregoing will be better understood with reference to the following examples that detail certain procedures for the preparation of kits and compositions according to the present invention. All references made to these examples are for the purposes of illustration. The following examples should not be considered exhaustive, but merely illustrative of only a few of the many embodiments contemplated by the present invention.

Example 1

Poly(d,l-lactide) (R 202H from Böhringer Ingelheim) in powder form and the solvent 2-pyrrolidone are separately filled in two syringes. The polymer is at least partially dissolved after connecting the syringes with a connector by pushing the syringe plungers forward and backward. The final polymer concentration in the carrier phase was 30% w/w. 130 mixing cycles (1 sec/cycle, 1 cycle equivalent to pushing the plungers forward and backward) were needed to obtain a polymer solution with the polymer powder used as received from the supplier. Milled polymer powder dissolved within 20 mixing cycles. Accordingly, a dissolution period of about 20 sec was obtained. Alternatively, the carrier phase can also be prepared within in a multi-chamber syringe. The polymer solution hardens in contact with pH 7.4 buffer, which simulates body fluids, and precipitates. The invention provides implants and particles that harden when exposed to a body fluid or physiological environment.

The carrier phase of above (in one syringe) is also dispersed in an external peanut oil phase, containing a stabilizer, if necessary, in a second syringe through a connector. The carrier phase hardens in contact with pH 7.4 buffer.

Example 2

Poly(d,l-lactide) (PLA) (R 202 H, RG 752, RG 503, RG 503H from Böhringer Ingelheim) in solid form is obtained by lyophilization of an organic PLA-solution (e.g., in DMSO, dioxane, ethyl lactate or acetic acid at a concentration of 10 to 30% w/w) within one syringe which is then stored separately from the solvents 2-pyrrolidone, N-methyl-pyrrolidone, ethyl acetate or triacetin. The polymer is at least partially dissolved by the solvent after connecting the syringes with a connector and pushing the syringe plungers forward and backward. 10 to 50 cycles were needed to form the carrier phase with the different polymers and solvents. The final polymer concentration in the carrier phase was between 10 and 40% w/w. The polymer dissolved fastest (less mixing cycles needed) in ethyl acetate>N-methyl-pyrrolidone>2-pyrrolidone>triacetin.

Accordingly, dissolution periods of less than 1 min or between 10 to 50 seconds were achieved. Alternatively, the carrier phase can also be prepared within in a multi-chamber syringe. The polymer solution hardens in contact with pH 7.4 buffer and precipitates.

The carrier phase of above (in one syringe) is also dispersed in an external peanut oil phase or water phase, containing a stabilizer, if necessary, (in a second syringe) through a connector. The carrier phase hardens in contact with pH 7.4 buffer.

Example 3

Poly(oxyethylene-oxypropylene) (Lutrol F127, BASF) powder [alternatively, poly(oxyethylene-oxypropylene) is obtained in solid form by lyophilization of an aqueous poly (oxyethylene-oxypropylene) solution) within a syringe] and water are separately filled in two syringes. The polymer is at least partially dissolved by the water after connecting the syringes with a connector and pushing the syringe plungers forward and backward. Alternatively, the carrier phase can also be prepared within in a multi-chamber syringe. Increasing the temperature to 37° C. leads to an increase in the viscosity of the polymer phase.

The carrier phase of above (in one syringe) is also dispersed in an external peanut oil phase, containing a stabilizer, if necessary, (in a second syringe) through a connector. Increasing the temperature to 37° C. leads to an increase in the viscosity of the carrier phase.

Example 4

Chitosan or a chitosan salt (e.g., chitosanglutamate) in powder form and an aqueous phase (slightly acidified in the case of chitosan) are filled separately in two syringes. Alternatively, chitosan in solid form can be obtained by lyophilization of an aqueous chitosan solution within a syringe). The polymer is at least partially dissolved after connecting the syringes with a connector and pushing the syringe plungers forward and backward. Chitosan precipitates in contact with pH 7.4 buffer.

The carrier phase of above (in one syringe) is also dispersed in an external peanut oil phase, containing a stabilizer, if necessary, (in a second syringe) through a connector. Chitosan precipitates in contact with pH 7.4 buffer.

Example 5

A monoglyceride (glycerolmonoleate, -linoleate, Myverol 18-92 or 18-99, or GMOrphic80) and a water-ethanol mixture are filled separately in two syringes. The monoglyceride is at least partially dissolved in the water-ethanol mixture after connecting the syringes with a connector and pushing the syringe plungers forward and backward. Viscous liquid crystalline phases, for example a cubic phase, form in contact with pH 7.4 buffer.

Example 6

The drug (doxycycline or lidocaine or leuprolide acetate) is added in powder form to the carrier materials, which are mentioned in the examples above, or is dried together with a solution of the carrier material, which are mentioned in the examples above, by lyophilization. The drugs were released from the formulations listed in Examples 1 and 2 over periods of several weeks up to 3 months. The invention provides extended release implants and particles that can release active compound over a period of up to six months. Formulations according to the invention provide an extended release of active compound for periods of up to one day, three days, one week, two weeks, one month, three months, or six months. The formulations begin to release drug shortly (less than one day, less than twelve hours or less than one hour) or immediately after installation in a site of use.

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

What is claimed is:

1. A kit for the preparation of a composition comprising a carrier phase, which forms an implant or particles in a body, on a body or under physiological conditions, the kit comprising: a first container containing at least one solid or semisolid carrier material; and a second container containing an amount of solvent sufficient to dissolve the carrier material, wherein the carrier material is separate from the solvent; wherein the carrier material is sufficiently soluble in the solvent so that it dissolves in the solvent within less than 60 minutes, if placed in contact and mixed therewith, thereby rapidly forming an administrable carrier phase comprising a polymer solution; the carrier material is a powder or lyophile; the solvent comprises water and/or one or more water-miscible organic solvents when the carrier material is water soluble; the solvent comprises one or more organic solvents when the carrier material is water insoluble; and wherein the administrable carrier phase forms an implant or particles in situ after being placed in a body, on a body or under physiological conditions.

2. A kit according to claim 1, wherein the carrier material and the solvent are stored in separate syringes or in separate chambers of a multi-chamber syringe such that when the carrier material is mixed with the solvent, prior to administration, through a connector or within a multi-chamber syringe, the carrier material is at least partially dissolved in the solvent.

3. A kit according to claim 1 or 2, wherein the carrier material comprises a water-soluble polymer, a water-insoluble polymer, a polymer that is soluble in aqueous fluids, a biocompatible and/or biodegradable polymer, a protein, a lipid, a non-polymeric material or a combination thereof.

4. A kit according to claim 3, wherein the carrier material comprises a poly(lactide) or poly(lactide)-derivative or copolymer, a monoglyceride, sucroseacetateisobutyrate or a combination thereof.

5. A kit according to claim 3, wherein the composition forms cubic or liquid crystalline phases in the body, on the body or under physiological conditions.

6. A kit according to claim 3, wherein the solvent is water or an organic solvent selected from the group consisting of ethanol, acetone, butanol, ethylformate, acetic acid, pentanol, n- or iso-propanol, tetrahydrofuran, triethylcitrate, triacetin, propylene glycol, glycerol, polyethylene glycol, ethylacetate, methylacetate, ethyllactate, benzylalcohol, dimethylformamide, dimethylsulfoxide, dimethylacetamide, propylenecarbonate, glycofurol, oleic acid, 2-pyrrolidone, N-methyl-2-pyrrolidone, an oil, a plasticizer and a mixture of two or more of these solvents.

7. A kit according to claim 3, wherein a portion of the carrier material is present in the solvent prior to mixing of the solvent with the solid carrier material.

8. A kit according to claim 3, wherein the composition further comprises at least one active compound.

9. A kit according to claim 8, wherein the active compound is encapsulated.

10. A kit according to claim 8, wherein the active compound in the kit is mixed with the carrier material, is present in the solvent or both.

11. A kit according to claim 8, wherein the composition further comprises a viscosity-modifying substance, stabilizer, release modifying agent, pore-former, substance that changes the residence time of the active compound or composition at a site of administration, bioadhesive material, penetration enhancer, substance for the retardation of the release of active compound, substance for the avoidance of a rapid initial release of active compound at a site of administration or a combination thereof.

12. A kit according to claim 8, wherein the composition is adapted for parenteral, peroral, subcutaneous, rectal, buccal, ophthalmic, pulmonary, vaginal, nasal, local, sublingual, periodontal, or transdermal administration, for application into a body cavity or for application onto a body surface.

13. A kit according to claim 8, wherein the composition is adapted for the treatment of soft- and hard tissue defects, treatment of tissue regeneration, use as glue, filling of a body cavity, or the treatment of a wound.

14. A kit according to claim 8, wherein the composition further comprises an additional liquid phase in which the administrable carrier phase can be dispersed to form a dispersion.

15. A kit according to claim 14, wherein the additional liquid phase is stored in the kit separate from the carrier material and the solvent, is in contact with the carrier material and separate from the solvent, or is in contact with the solvent and separate from the carrier material.

16. A kit according to claim 14, wherein the additional liquid phase comprises natural, semisynthetic or synthetic lipids, oils or waxes; triglyceride mixture; monoglyceride; silicone oil; isopropylmyristate; ethyloleate; paraffin; water; glycerol; propylene glycol; polyethylene glycol; or a mixture thereof.

17. A kit according to claim 14, wherein the at least one active compound is present together with one or more of the carrier material, solvent or additional liquid phase.

18. A method for the preparation of a kit, the method comprising the steps of:
including a carrier material in solid or semisolid form in a syringe or in a chamber of a multi-chamber syringe, wherein the carrier material is a powder or lyophile; and
including a solvent for the carrier material in a separate syringe or separate chamber of the multi-chamber syringe, wherein the solvent comprises one or more water and/or one or more water-miscible organic solvents when the carrier material is water soluble; the solvent comprises one or more organic solvents when the carrier material is water insoluble;
wherein the solvent is present in an amount sufficient to dissolve the carrier material, the carrier material is sufficiently soluble in the solvent so that it dissolves in the solvent within less than 60 minutes when placed in contact therewith and mixed to rapidly form an administrable carrier phase, and the administrable carrier phase forms an implant or particles in situ after being placed in a body, on a body or under physiological conditions.

19. A method according to claim 18, the step of including the carrier material comprises the step of:
placing the carrier material in solution or dispersion form in the syringe or the chamber of the multi-chamber syringe; and
drying or lyophilizing the carrier material to form a solid or semisolid.

20. A method according to claim 18 or 19, wherein the carrier material is a water-soluble polymer, a water-insoluble polymer, a polymer that is soluble in aqueous fluids, a biocompatible and/or biodegradable polymer, a protein, a lipid, a non-polymeric material or a combination thereof.

21. A method according to claim 18 or 19 further comprising the step of:
including at least one active compound present separately, mixed with the carrier material, mixed with the solvent or mixed with both the carrier material and the solvent such that the at least one active compound is included within the carrier phase.

22. A method according to claim 18 or 19 further comprising the step of:
including an additional liquid phase for dispersion of the carrier phase when mixed therewith, wherein the additional liquid phase is stored in the kit separate from the carrier material and the solvent, is in contact with the carrier material and separate from the solvent, or is in contact with the solvent and separate from the carrier material.

23. A method according to claim 22 further comprising the step of:
including at least one active compound present separately, or present as a mixture with the carrier material, solvent, additional liquid phase or a combination thereof such that the at least one active compound is included within the carrier phase and/or additional liquid phase.

24. A method for the preparation of an implant or particulate composition in situ after being placed in a body, on a body or under physiological conditions, the method comprising the steps of:
providing at least one solid or semisolid carrier material and solvent in separate syringes or separate compartments of a multi-compartment syringe, wherein carrier material is a powder or lyophile, the solvent is present in an amount sufficient to dissolve the carrier material if placed in contact and mixed therewith, the solvent comprises water and/or one or more water-miscible organic solvents when the carrier material is water soluble, the solvent comprises one or more organic solvents when the carrier material is water insoluble;
mixing the carrier material and solvent such that the carrier material dissolves in the solvent within less than 60 minutes thereby forming an administrable carrier phase; and
administering the carrier phase by placing it within or on a subject or by exposing it to a physiological condition thereby forming the implant or particulate composition in situ.

25. A method according to claim 24, wherein the carrier material is a water-soluble polymer, a water-insoluble polymer, a polymer that is soluble in aqueous fluids, a biocompatible and/or biodegradable polymer, a protein, a lipid, a non-polymeric material or a combination thereof.

26. A method according to claim 24 or 25 further comprising the step of:
including at least one active compound present separately, mixed with the carrier material, mixed with the solvent or mixed with both the carrier material and the solvent.

27. A method according to claim 24 or 25 further comprising the step of:
including an additional liquid phase, wherein the additional liquid phase is stored in the kit separate from the carrier material and the solvent, is in contact with the carrier material and separate from the solvent, or is in contact with the solvent and separate from the carrier material; and the additional liquid phase forms a particulate dispersion with the carrier phase when mixed therewith.

28. A method according to claim 27 further comprising the step of:
including at least one active compound present separately, or present as a mixture with the carrier material, solvent, additional liquid phase or a combination thereof.

29. A kit according to claim 8, wherein the implant or particles provide an extended release of active compound when placed in the body, on the body or under physiological conditions.

30. A kit according to claim 14, wherein the implant or particles provide an extended release of active compound when placed in the body, on the body or under physiological conditions.

31. A method according to claim 21, wherein the carrier phase provides an extended release of active compound when placed in a body, on a body or under physiological conditions.

32. A method according to claim 23, wherein the carrier phase provides an extended release of active compound when placed in a body, on a body or under physiological conditions.

33. A method according to claim 26, wherein the implant or particles provide an extended release of active compound.

34. A method according to claim 28, wherein the implant or particles provide an extended release of active compound.

35. A kit according to claim 2, wherein at least 75% wt. of the carrier material dissolves in the solvent to form the polymer solution.

36. A kit according to claim 35, wherein the carrier material dissolves in the solvent in less than 5 minutes.

37. A kit according to claim 35, wherein the carrier material dissolves in the solvent in less than 30 minutes.

38. A kit according to claim 35, wherein the carrier material dissolves in the solvent in less than 20 minutes.

39. A kit according to claim 35, wherein the carrier material dissolves in the solvent in less than 10 minutes.

40. A kit according to claim 35, wherein the carrier material dissolves in the solvent in less than 1 minute.

41. A kit according to claim 1, wherein the carrier material is porous.

* * * * *